(12) United States Patent
West

(10) Patent No.: US 6,579,995 B1
(45) Date of Patent: Jun. 17, 2003

(54) PROCESS FOR PHOSPHORYLATION AND COMPOUNDS PRODUCED BY THIS PROCESS

(75) Inventor: Simon Michael West, Williamstown (AU)

(73) Assignee: Vital Health Sciences Pty Ltd, Melbourne (AU)

( * ) Notice: Subject to any disclaimer, the term of this patent is extended or adjusted under 35 U.S.C. 154(b) by 0 days.

(21) Appl. No.: 09/979,436

(22) PCT Filed: May 12, 2000

(86) PCT No.: PCT/AU00/00452

§ 371 (c)(1),
(2), (4) Date: Nov. 14, 2001

(87) PCT Pub. No.: WO00/69865

PCT Pub. Date: Nov. 23, 2000

(30) Foreign Application Priority Data

May 14, 1999 (AU) .............................................. PQ 0374
Jan. 25, 2000 (WO) ............................... PCT/AU00/00038

(51) Int. Cl.[7] .............................. C07J 1/00; C07J 9/00; C07J 211/00; C07D 205/00
(52) U.S. Cl. ....................... 552/544; 552/625; 548/952; 564/374
(58) Field of Search ................................ 552/544, 625; 548/952; 564/374

(56) References Cited

U.S. PATENT DOCUMENTS

| | | | | |
|---|---|---|---|---|
| 4,141,938 | A | | 2/1979 | Klose .......................... 260/928 |
| 4,874,883 | A | | 10/1989 | Uphues et al. .............. 558/150 |
| 5,138,084 | A | * | 8/1992 | Casagrande et al. ........ 558/110 |
| 5,554,781 | A | * | 9/1996 | Reierson ..................... 558/110 |
| 5,741,518 | A | * | 4/1998 | Ribier et al. ................ 424/450 |
| 5,759,526 | A | * | 6/1998 | Simonnet et al. ............. 424/59 |
| 5,804,216 | A | * | 9/1998 | Terren et al. ................ 424/450 |

FOREIGN PATENT DOCUMENTS

| | | |
|---|---|---|
| JP | 84-259538/42 | 9/1984 |
| JP | 87-281015/40 | 8/1987 |
| JP | 96-055975/06 | 12/1995 |
| JP | 96-397241/40 | 7/1996 |
| JP | 97-061803/06 | 11/1996 |

* cited by examiner

Primary Examiner—Barbara P. Badio
(74) Attorney, Agent, or Firm—Dorsey & Whitney LLP

(57) ABSTRACT

The present invention is directed to improved processes for phosphorylation and compounds produced by the improved processes. The improved process for phosphorylating complex alcohols comprises the following steps: (a) forming an intimate mixture of one or more complex alcohols and $P_4O_{10}$ at a temperature below 80° C. in the absence of additional solvents; and (b) allowing the intimate mixture to continue to react for a period of time at a temperature below 80° C. until the formation of the dihydrogen form of the phosphorylated complex alcohol is substantially completed.

10 Claims, No Drawings

PROCESS FOR PHOSPHORYLATION AND COMPOUNDS PRODUCED BY THIS PROCESS

CROSS-REFERENCE TO RELATED APPLICATIONS

This application is a national stage filing based upon international application no. PCT/AU00/00452, filed May 12, 2000 and published in English on Nov. 23, 2000 as international publication no. WO 00/69865 (the '452 application), which claims priority to Australian application no. PQ0374, filed May 14, 1999 (the '374 application), and international application no. PCT/AU00/00038, filed Jan. 25, 2000 (the '038 application). The '452, '374, and '038 applications are hereby incorporated by reference as though fully set forth herein.

FIELD OF THE INVENTION

The invention relates to an improved process for phosphorylation of organic hydroxyl groups and the compounds produced using this process.

BACKGROUND OF THE INVENTION

In this specification, where a document, act or item of knowledge is referred to or discussed, this reference or discussion is not to be taken as an admission that the document, act or item of knowledge or any combination thereof was at the priority date:

(a) part of common general knowledge; or (b) known to be relevant to an attempt to solve any problem with which this specification is concerned.

Whilst the following discussion highlights the invention with respect to dietary supplements, it is believed that the same principles apply to other compounds containing organic hydroxyl groups such as pharmaceutical compounds with hydroxyl groups.

The use of dietary supplements is well known, for example hormones, phytosterols or chromans. One of the problems encountered with such supplements for human ingestion is that many of the supplements are relatively water insoluble but the human digestive tract is a substantially aqueous system. Previous attempts to overcome this problem include using emulsifiers to enable an oil-based solution of the supplement to combine with an aqueous system and thus maintain the supplement's bioavailability. Consequently, it would be useful to be able to convert these dietary supplements to water soluble compounds without disturbing their inherent structure. Phosphate salts with either potassium or sodium are already found in biological tissue. Therefore phosphate salts should be tolerated by the body.

There is a diverse art for the production of organic phosphates, however none of these methods are considered to be suitable for production of complex phosphate compounds because they are either unsuitable for use on a commercial scale or there are side reactions which produce undesired by-products.

Ordinarily, phosphorylation reagents and methods are chosen to avoid significant degradation of the compound being phosphorylated. Where gentle conditions are required, then reagents such as 2:2:2-trichloroethyl dichlorophosphate, di-imidazolide chlorophosphate and di-analide chlorophosphate have been employed but have limited yields which are inadequate for commercial processes. When more severe conditions are feasible, then phosphorous oxychloride has been used, but the reaction produces a variety of by-products together with hydrogen chloride. There are other problems associated with the fact that phosphorous oxychloride is difficult to manage which make this reagent unsuitable for use on a commercial scale.

Although $P_4O_{10}$ [which is often incorrectly called phosphorous pentoxide] has been used for phosphorylation of ethanol and other short chain primary alcohols, it has not been used for higher alcohols and complex molecules because the temperatures used are too high and there is considerable degradation. Another reason why $P_4O_{10}$ is not used for higher alcohols and complex molecules is that at the higher temperatures used in known $P_4O_{10}$ processes, there is formation of a significant amount of by-products. Even with ethanol, there is a significant amount of diethylphosphate as well as monoalkylphosphate which is produced and these substances must be removed. Commercial processes use $P_4O_{10}$ with ethanol but there is a complicated clean-up procedure because the reaction occurs at a high temperature.

Further, with secondary or tertiary alcohols $P_4O_{10}$ causes dehydration and formation of a double bond. This dehydration is further promoted by the high temperatures at which this reaction takes place. In fact, this is a standard reagent and method for forming a double bond. This reaction has thus been considered to be unsuitable for production of complex phosphate compounds.

It is the need for lower temperatures which has led to the use of $POCl_3$ because, in the presence of a base, a lower temperature can be used and degradation is avoided. $POCl_3$ is the preferred method for phosphorylating complex molecules.

There is, therefore, a need for a reliable process for phosphorylating complex compounds so that these compounds can be used in aqueous environments.

SUMMARY OF THE INVENTION

It has surprisingly been found that $P_4O_{10}$ can be used to phosphorylate primary fatty alcohols, secondary alcohols (including cyclohexanols) and aromatic alcohols (including phenols and chromanols). In this description and in the claims, the term "complex alcohols" refers to primary fatty alcohols, secondary alcohols and aromatic alcohols. The complex alcohols include hormones, phytosterols, tocopherols (chromans), vitamin K1 and other oil-soluble vitamins and dietary supplements as well as pharmaceutical compounds such as Amoxycillin.

In this description, the word "intimate" is used to signify its technical meaning as known to persons skilled in the art. That is, to signify that two substances are in very close physical contact dispersed as particles which are as small as possible so that a reaction is initiated. There must be as large a surface area as possible for the reaction to initiate and this is also advantageous for further reaction.

Accordingly, there is provided a process for phosphorylating complex alcohols comprising the following steps:

(a) forming an intimate mixture of one or more complex alcohols and $P_4O_{10}$ at a temperature below 80° C. in the absence of additional solvents; and (b) allowing the intimate mixture to continue to react for a period of time at a temperature below 80° C. until the formation of the dihydrogen form of the phosphorylated complex alcohol is substantially completed.

It is understood that in steps (a) and (b), the temperature is sufficient to ensure there is minimum degradation of the complex alcohols but the reaction will still proceed to a satisfactory extent.

The complex alcohols must be in a liquid phase at the desired temperature of reaction. Persons skilled in the art will be aware that some complex alcohols are commercially supplied in a stabilizing medium. Such complex alcohols may be used in this process without removing the stabilizing medium.

Preferably, where minimum degradation is desired, the temperature at which the reaction is performed is in the range from 0 to 50° C. More preferably, the temperature is in the range from 0 to 40° C.

Preferably where the period of time in step (b) is minimized, the temperature at which the reaction is performed is about 70° C.

The ratio of $P_4O_{10}$ to complex alcohols will depend on the temperature at which the reaction occurs. At the higher temperatures, the ratio of phosphorus to complex alcohols is substantially equimolar. That is, at the higher temperatures there is more efficient consumption of the phosphate groups. At the lower temperatures, the ratio of $P_4O_{10}$ to complex alcohols is substantially equimolar.

The period of time in step (b) is dependent on the temperature at the ratio of reagents. Where there is equimolar phosphorus, preferably the period of time does not exceed about 30 minutes. Where there is equimolar $P_4O_{10}$, preferably the period of time does not exceed about 10 minutes.

The choice of temperature at which the reaction occurs is dependent on the expense of the complex alcohols. For example, Amoxycillin is expensive therefore it is preferable to minimize the degradation of Amoxycillin.

Where lower temperatures are used and there are unreacted reagents, the unreacted reagents can be recycled. For example, if the temperature is between 0 to 40° C., the process would further comprise a step where the unreacted reagents were mixed with more $P_4O_{10}$ and complex alcohol and steps (a) and (b) repeated.

The phosphorylated complex alcohols may be recovered as either the acid or as a salt (usually potassium or sodium) using methods known to those skilled in the art. For example, the reaction mixture from step (b) may be neutralized with potassium or sodium hydroxide then the water evaporated to recover the salt.

The pressure is typically at atmospheric because there is no advantage using higher pressures at these temperatures.

The intimate mixture is formed using methods known to those skilled in the art. Vigorous stirring is typically necessary to achieve an intimate mixture. In a laboratory, a mortar and pestle can be used. In an industrial plant, a high shear mixer would be used.

According to a preferred embodiment, formation of the intimate mixture in step (a) is performed in the presence of an aliphatic carboxylic acid excluding formic and acetic acid. In this description and in the claims, the term "aliphatic acid" refers to any aliphatic carboxylic acid except for formic acid and acetic acid. Preferably, the aliphatic acid is a free fatty acid. Examples include oleic acid and stearic acid. The aliphatic acid acts as a catalyst for the reaction and reduces the side reactions.

According to another form of the invention, there is provided a phosphate derivative of a complex alcohol which was produced by the above process.

EXAMPLES

The invention will now be further explained and illustrated by reference to the following non-limiting examples.

Example 1

$P_4O_{10}$ (0.28 g) was added to 1-dodecanol (0.18 g) and stearic acid (0.02 g). The mixture was stirred vigorously for 5 mins at 20–25° C. The product was analyzed by electrospray mass spectrometry which showed the formation of 1-dodecanol phosphate.

Example 2

A phytosterol extract containing mainly beta sitosterol, stimasterol and campastenol (0.4 g) was mixed with polyphosphoric acid (0.8 g) at 20–25° C. by grinding in a mortar and pestle for 0.5 hours then let stand for 12 hours at ambient temperature. The product was diluted with acetonitrile and then analyzed by spray mass spectrometry which showed that the mono-phosphates of the sterols were present.

Example 3

17 beta-estradiol (0.27 g) was mixed with polyphosphoric acid (0.3 g) at 20–25° C. in a mortar and pestle for 0.5 hours then let stand for 12 hours at ambient temperature. The product was diluted with acetonitrile and analyzed by spray mass spectrometry which showed that 17 beta-estradiol monophosphate had been formed.

Example 4

Alpha-phylloquinone (or vitamin K1) (0.45 g in 5 g oleic acid) was mixed with $P_4O_{10}$ at 20–25° C. in a mortar and pestle for 0.5 hours then let stand for 12 hours at ambient temperature. The product was analyzed which showed that the mono-phosphate was formed.

Example 5

$P_4O_{10}$ (165.1 g) was added to tocopherol (1 kg) and stirred together for 30 minutes at 70° C. The mixture discoloured to give a brown/black material which became very viscous. The material was then mixed vigorously with a mechanical stirrer for 30 minutes in water (10 l) to form a slurry. The slurry was then centrifuged, the water discarded, and the pellet collected. The pellet was then dissolved in AR ethanol (10 l). Then sodium (160.4 g) was added slowly to the solution and stirred by a magnetic stirrer. The mixture was then filtered, resuspended in AR ethanol (10 l) and heated to reflux, so dissolving the unreacted tocopherol and fatty acid. The hot dispersion was cooled and filtered to recover di-sodium tocopherol phosphate.

Example 6

$P_4O_{10}$ (3.0 g)was added to a mixture of dopamine hydrochloride (2.0 g) and stearic acid (0.04 g), then mixed together. To the resulting heterogenous solid was added water (0.3–0.5 ml), causing an exothermic reaction (~50° C.). The resulting slurry was stirred for 2–3 minutes, then water (50 ml) was added completely dissolving the mixture. The mixture was analyzed using electro-spray mass spectrometry to find dopamine phosphate and inorganic phosphates.

Example 7

The above procedure (example 6) was repeated with amoxicillin.trihydrate (2 g), stearic acid (0.04 g) and $P_4O_{10}$ (1.4 g). The product mixture contained Amoxicillin phosphate and inorganic phosphates.

Example 8

The above procedure (example 6) was repeated with cholesterol (2.0 g), stearic acid (0.04 g) and $P_4O_{10}$ (1.5 g). The reaction mixture was dispersed into water (50 ml) then centrifuged to recover the cholesterol phase. This phase was analyzed and was found to contain unreacted cholesterol and cholesterol phosphate.

The novel process for phosphorylation has been successfully used for a variety of useful compounds and would be understood by those skilled in this art to have an obviously wider application.

The word comprising and forms of the word comprising as used in this description and in the claims does not limit the invention claimed to exclude any variants or additions.

Modifications and improvements to the invention will be readily apparent to those skilled in the art. Such modifications and improvements are intended to be within the scope of this invention.

What is claimed is:

1. A process for phosphorylating complex alcohols comprising the following steps:
   (a) forming an intimate mixture of one or more complex alcohols and $P_4O_{10}$ at a temperature below 80° C. in the absence of additional solvents; and
   (b) allowing the intimate mixture to continue to react for a period of time at a temperature below 80° C. until the formation of the dihydrogen form of the phosphorylated complex alcohol is substantially completed.

2. A process according to claim 1 wherein the temperature in steps (a) and (b) is in the range from 0 to 50° C.

3. A process according to claim 2 wherein the temperature in steps (a) and (b) is in the range from 0 to 40° C.

4. A process according to claim 1 wherein the temperature in steps (a) and (b) is about 70° C.

5. A process according to any one of claims 1 or 4 wherein the ratio of phosphorus to complex alcohols is substantially equimolar.

6. A process according to any one of claims 2 or 3 wherein the ratio of $P_4O_{10}$ to complex alcohols is substantially equimolar.

7. A process according to claim 5 wherein the period of time in step (b) does not exceed about 30 minutes.

8. A process according to claim 6 wherein the period of time in step (b) does not exceed about 10 minutes.

9. A process according to claim 1 wherein the intimate mixture in step (a) is formed in the presence of an aliphatic acid.

10. A process according to claim 9 wherein the aliphatic acid is a free fatty acid.

* * * * *